United States Patent [19]

Beavers et al.

[11] Patent Number: 5,789,571
[45] Date of Patent: Aug. 4, 1998

[54] METHOD OF MAKING FREE ACIDS FROM POLYSACCHARIDE SALTS

[75] Inventors: Ellington M. Beavers, Meadowbrook; Djoerd Hoekstra, Malvern; Yee San Su, Fort Washington; Nicole Willard, Collegeville, all of Pa.

[73] Assignee: Biocoat Incorporated, Pa.

[21] Appl. No.: 781,308

[22] Filed: Jan. 15, 1997

[51] Int. Cl.$^6$ .............. C07H 1/06; C07H 13/02; C07H 1/00
[52] U.S. Cl. .............. 536/124; 536/119; 536/127
[58] Field of Search .............. 536/124, 127, 536/119

[56] References Cited

U.S. PATENT DOCUMENTS 4,589,963 5/1986 Cipriano et al. .............. 204/72
4,736,024 4/1988 Della Valle et al. .............. 536/55.3
5,268,079 12/1993 Gomez et al. .............. 204/182.4
5,532,221 7/1996 Huang et al. .............. 536/119

*Primary Examiner*—John Kight
*Assistant Examiner*—Everett White
*Attorney, Agent, or Firm*—William H. Eilberg

[57] ABSTRACT

A free acid form of a polysaccharide is produced from its alkali-metal salt. In one example, free-form hyaluronic acid is produced by preparing a solution of an alkali-metal salt of hyaluronic acid, dispersing into the solution a strong acid, enclosing the dispersion within a semi-permeable membrane, dialyzing the dispersion in water, and harvesting the product from within the membrane. The strong acid can be hydrochloric acid, sulfuric acid, nitric acid, orthophosphoric acid, or oxalic acid, for example. The semi-permeable membrane has a molecular weight cut-off large enough to pass the strong acid, and preferably much larger. The invention provides a simple and economical way to produce a product which is not commercially available.

20 Claims, No Drawings

METHOD OF MAKING FREE ACIDS FROM POLYSACCHARIDE SALTS

BACKGROUND OF THE INVENTION

The present invention provides a method of making free acids from polysaccharide salts. The invention is especially useful in making pure hyaluronic acid.

Polysaccharides have been shown to be useful in making hydrophilic, lubricious coatings on substrates. Such coatings are described in U.S. Pat. Nos. 4,801,475, 5,023,114, and 5,037,677, the disclosures of which are hereby incorporated by reference. In general, these patents disclose bilaminar coatings comprising a primary coat which adheres tightly to a plastic substrate, and a top-coat which comprises a polysaccharide which is hydrophilic, lubricious and durable. The primary coat and the top-coat are grafted together with covalent bonds, and retain their individual identities even after grafting. The bilaminar coatings can be used on catheters, guide wires, prosthetic devices, intra-ocular lenses, or other devices which are permanently or temporarily inserted into the body.

The preferred polysaccharide described in the above-cited patents is sodium hyaluronate. Sodium hyaluronate was first isolated and identified chemically as a polysaccharide in the early 1930s. It occurs in nature, has never been synthesized, and is a component of the mammalian system, occurring in especially high concentration in the mucosa, in the umbilical cord, and at the body's movable joints. Although it is commercially available as the sodium salt, it is commonly spoken of as "hyaluronic acid" and in everyday parlance as "HA". In most cases, the sodium salt is entirely satisfactory for the role it is called upon to play. Indeed, other salt forms, such as the potassium salt, may be irritating to some membranes and even toxic.

However, for important new uses of the polysaccharide, the free-acid form is needed, as for example when the carboxyl group is required to participate in chemical reactions that do not proceed with the sodium salt. This requirement poses a quandary, because the industrial processes for salt splitting cannot be applied economically to the extremely viscous aqueous solutions of sodium hyaluronate having molecular weights of a million and more. Not only are such solutions extremely viscous, but they also display non-Newtonian, thixotropic flow, and as semi-gels do not flow readily under hydrostatic pressure.

Although its sodium salt is commercially available, free hyaluronic acid is not an article of commerce. Moreover, it is believed, after considerable investigation, that the free acid is not commercially available, and never has been commercially available. The same is believed to be true in the case of other polysaccharides such as chondroitin sulfate, heparin, and carboxymethyl cellulose.

The present invention therefore has the purpose of providing a pure acid form of a polysaccharide, such as hyaluronic acid, by a practical and economical procedure. The invention can thereby provide a substance which has not been produced.

SUMMARY OF THE INVENTION

The present invention produces a pure acid form of a polysaccharide by strongly acidifying an aqueous solution of an alkali-metal salt of the polysaccharide, and then removing the acid through a semi-permeable membrane.

In the preferred embodiment, the polysaccharide is sodium hyaluronate. The process is conducted by dissolving an alkali-metal salt of hyaluronic acid in water, dispersing, in the solution, an acid capable of producing a pH of 2.2 or lower at concentrations in water at 25° C. of 0.01 Normal to 1 Normal, dialyzing in water the above dispersion which is enclosed in a semi-permeable membrane having a molecular weight cut-off at least large enough to pass the acid added, and then harvesting the product. The process is similar when conducted with other polysaccharides.

The invention also comprises the product made by the process described above, namely pure hyaluronic acid (HA) or the free acid form of another polysaccharide.

The present invention therefore has the primary object of providing a process for making a free acid form of a polysaccharide.

The invention has the further object of making pure hyaluronic acid (HA) from sodium hyaluronate.

The invention has the further object of providing a practical and economical source of pure hyaluronic acid for applications in which the pure form of the acid is required.

The invention has the further object of converting an alkali-metal salt of hyaluronic acid to the free acid form, in as chemically pure and contaminant-free condition as the original salt, or in better condition.

The invention has the further object of providing pure hyaluronic acid which readily undergoes chemical reactions with substances such as 1,2-epoxides, aziridines, and alcohols, under conditions in which sodium hyaluronate is inert.

The invention has the further object of providing a component used in making hydrophilic, lubricious, and durable coatings for devices which are intended to be placed permanently or temporarily in the body.

The reader skilled in the art will recognize other objects and advantages of the present invention, from a reading of the following detailed description of the invention, and the appended claims.

DETAILED DESCRIPTION OF THE INVENTION

The method of the present invention comprises the basic steps of strongly acidifying an aqueous solution of an alkali-metal salt of a polysaccharide, and then removing the acid through a semi-permeable membrane. The pure acid form is then harvested from the interior of the membrane.

In the preferred embodiment, the polysaccharide is sodium hyaluronate, and the method of the present invention produces substantially pure hyaluronic acid. The following Example shows basic details of the method.

EXAMPLE 1

A greater-than-stoichiometric amount of hydrochloric acid was added to a solution of sodium hyaluronate, and the mixture was then sealed in dialysis tubing having a molecular weight cutoff (MWCO) higher than 36.5. The bag was immersed in distilled water. The pH of the water outside the bag dropped quickly to a level of approximately 2.5–3 as the mineral acid was extracted. The external water was changed periodically until its pH no longer indicated that acid was being extracted. The hyaluronic solution in the bag was harvested at this point and was found to be free of chloride ion by a test with silver nitrate solution.

The material harvested was shown to be a solution of hyaluronic acid having a pH of 3.0–3.5. Its viscosity was slightly lower than the original value, because of some dilution that occurred from osmosis of water through the membrane into the bag. No other changes in physical or chemical properties were apparent, as compared with those of the original material. The product readily undergoes chemical reactions with 1,2-epoxides, aziridines, and alcohols under conditions in which the original sodium hyaluronate is inert. This new versatility gives the product commercial value not possessed by sodium hyaluronate.

The addition of hydrochloric acid to the viscous solution of sodium hyaluronate causes a marked increase in viscosity of the solution. As the strong acid is added, the already viscous solution tends to become more viscous, even to the point of becoming a strong gel that undergoes shear only with forcing. Equipment such as a sigma-blade or dough mixer is available for handling materials of this kind.

The dialysis expert might try to overcome the above-described mechanical problem by using the process described in Example 2, as a means of acidifying without dealing with the viscosity phenomenon. As shown later, the latter approach does not give satisfactory results.

EXAMPLE 2

A 0.6% aqueous solution of sodium hyaluronate with a viscosity of 37 stokes was placed in a dialysis bag with MWCO of 2000. The bag was suspended in a one-tenth normal solution of hydrochloric acid, the solution having a measured pH of 1.4. For an equilibration period of at least 24 hours, no change in pH of the outer phase was observed. The outer phase was then replaced with de-ionized water and the process of Example 1 was then followed. The final harvested product had a pH of 3.0, an acid value of 0.455 equivalents per gram, and a negative test for chloride ion.

Although the product of Example 2 appears to have the same characteristics as the product of Example 1, the two behave quite differently in their reactions with carboxylic polymers as coatings, as shown in Example 3.

EXAMPLE 3

An emulsion copolymer of acrylic acid was mixed with Crosslinker CX-100 and deposited by coating knife at 6 mils wet on each of three acrylic panels 0.25 inches×2.5 inches× 6.5 inches in size. Crosslinker CX-100 is available from Zeneca Resins, of Wilmington, Massachusetts. The coating was air-dried for 2 hours. Each of the products of Example 1 (Case A) and Example 2 (Case B) was applied as a top-coat at 6 mils wet over the air-dried coatings. On the third acrylic panel, with an air-dried base coat, there was applied a solution of sodium hyaluronate (Case C) as in Cases A and B. The three panels were cured overnight at a temperature of 140° F. The panels were then placed in water in the pan of a BYK-Gardner abrasion tester fitted with a hog-bristle brush under a weight of one pound, and cycling was started. The coatings of Cases B and C failed, by loss of wettability, in fewer than 5000 cycles, whereas the panel of Case A was still in its original good condition after 250,000 cycles.

The basic reason for the large difference in performance between the panel of Case A, and those of Cases B and C, is not fully understood, but it is believed that part of the reason is that in the procedure of Example 2, a gel barrier may have formed early and prevented intimate mixing of the strong acid with the sodium hyaluronate in the dialysis bag. In Case C, the strong acid essential to the present invention was not present.

As explained above, one commercial application for hyaluronic acid in the free acid form is in the manufacture of hydrophilic, lubricious, bilaminar coatings, wherein both a primary coat and a polysaccharide top-coat are capable of reacting with a grafting agent that will tie them together with covalent bonds and prevent the top coat from being washed away in aqueous media such as water or blood. The first coat might be, for example, a copolymer of hydroxyethyl methacrylate supplied in an organic solvent such as methoxypropyl acetate, and a polyisocyanate can be used as the grafting agent. However, if the very same copolymer were made in aqueous emulsion, the polyisocyanates would either not be miscible with water or, if miscible with water, would react preferentially with the water solvent rather than in the desired manner with the hydroxyethyl methacrylate copolymer and the polysaccharide. Despite this problem, there is a strong incentive to use polymers in aqueous dispersions because of the ease of clean-up after use, and the absence of hazards of fire, explosion, and toxicity that are often present with organic solvents.

Instead of polyisocyanates, one can use polyfunctional 1,2-aziridines or 1,2-epoxides, for example, as grafting and crosslinking agents, in the presence of water, if the first-coat copolymer and the polysaccharide top-coat both contain free carboxyl groups for reaction with aziridine -or epoxide groups. The carboxyl functionality is readily supplied in the first coat by including acrylic or methacrylic acid, for example, as one of the comonomers in preparing the emulsion polymer. The carboxyl functionality in the polysaccharide top coat is supplied by the process of the present invention. As shown in Example 3, Crosslinker CX-100, a polyaziridine, is not effective in grafting the sodium salt of hyaluronic acid, and the top coat is therefore quickly washed away in the abrasion tester. As also shown in Example 3, a bilaminar coating of excellent lubricity and durability is obtained when free hyaluronic acid is used for the top coat.

Strong acids that are suitable are those that would produce a pH of 2.2 or lower at concentrations in water at 25° C. in the range of 0.01 Normal to 1 Normal. Thus, suitable acids are, for example, hydrochloric, sulfuric, nitric, orthophosphoric, and oxalic. Unsuitable acids, for example, are carbonic, hydrocyanic, acetic, or hydrogen sulfide. Acids that have the proper strength but also have strong oxidizing potential, such as certain peracids, should be avoided because of the possibility of undesirable side reactions.

Dialysis membranes made from regenerated cellulose or from cellulose esters are suitable for use in the present invention. Pore size, which determines the molecular weight cut-off, should be at least large enough to pass the strong acid used. Considerably larger MWCO should be selected in most cases for the practical reason that the dialysis rate is faster as the cut-off level is increased. For example, when hydrochloric acid is chosen as the strong acid, a membrane with a MWCO of 100 has a pore size adequate for passage of HCl, but other conditions being the same, a membrane with MWCO of 2,000 gives a dialysis rate four times faster.

Example 4 provides a further illustration of a typical operation of the process of the present invention. This example is only illustrative, and is not intended to limit the scope of the invention.

EXAMPLE 4

A solution of sodium hyaluronate was prepared at 0.6% concentration in distilled water. The viscosity of the sodium hyaluronate was 150 stokes at 25° C. While the solution was being mixed with a stainless steel agitator with a large perforated blade, 0.1N hydrochloric acid was added, in the proportion of 2.5 pounds per 100 pounds of hyaluronate solution. When the acid was first being added, the viscosity of the mix increased rapidly, and the material climbed the agitator shaft. Thermowells and other baffles promoted mixing nevertheless, and the addition of acid was continued to completion. The viscosity soon reverted to about the original level, and stirring was continued for one hour.

The solution was loaded into dialysis bags having a MWCO of 3500, and the bags were sealed and placed in de-ionized water. Within an hour, the pH of the external water bath had fallen to a value of 2.3. The water was replaced with fresh de-ionized water periodically, until the pH of the external water reached 5.4. A sample of the dialysed solution was tested with 5% silver nitrate solution and found to be free of chloride ion. The dialysed solution was harvested and analyzed with the following results:

| Viscosity, 25° C. | 27 Stokes |
| Concentration | 0.55% |
| pH | 3.2 |
| Appearance | Sparkling clear and colorless |

The specific details of processing will vary with the type of equipment used, the choices made of factors such as concentration of the original hyaluronate solution, the source and characteristics of the sodium hyaluronate used, the nature of the added acid, and its concentration and ratio to hyaluronate, etc. However, the general principles that should be considered in adapting the process to particular circumstances are the following:

1. The ratio of external water volume to hyaluronate solution volume should be kept as low as practical, preferably in the vicinity of 5/1 or lower.
2. An analytical tool is needed to detect the point at which the added acid has been adequately removed. As a first approximation, one can use the pH of the external bath as an indicator of this point.
3. For some applications, it will not be necessary, and perhaps not even desirable, to convert all of the salt forms in a given polysaccharide to the free carboxylic acid forms. In a sample of sodium hyaluronate with average molecular weight of 2 to 3 million, for example, only a few grafting points should be ample to anchor the top-coat to the primary coat, and a larger number of grafting points will diminish the potential lubricity of the final coating. To achieve less than complete conversion of salt forms to free-acid forms, the amount of strong acid added to the sodium polysaccharide solution will be adjusted to less than the stoichiometric amount. Whatever the ratio of strong acid added to achieve desired results, the process will be operated after the addition in the same manner as described above.
4. The temperature is not a critical factor, within limits. The process has been operated during winter and summer, and reaction rates are very similar at temperatures as low as about 4° C. and as high as about 30° C. The process therefore works essentially at any temperature that could be considered ambient.

The process of the present invention is not limited to use with hyaluronic acid, but has been demonstrated to be useful in converting the sodium salts of chondroitin sulfate, and of carboxymethyl cellulose, to the free acid. It should also be applicable to salts of heparin. The following examples show the results obtained with chondroitin sulfate and carboxymethyl cellulose.

EXAMPLE 5

A 10% aqueous solution was prepared from chondroitin sulfate isolated from shark cartilage, supplied by Marcor Corporation. While the solution was vigorously stirred, 6.6 grams of one-normal HCl per 100 grams of chondroitin sulfate solution was added dropwise. The uniform solution was sealed into dialysis tubing having a molecular weight cutoff of 500 and the tube was immersed in stirred de-ionized water. After two water changes, the pH of the external water was 7.0, and the product of the dialysis was harvested. Analysis of the product gave the following results:

| pH | 3.9 |
| Viscosity | 0.4 poise |
| AgNO$_3$ test for Cl$^-$ ion | Negative |
| Appearance | Clear, light amber |

The product could be gelled by reaction with Crosslinker CX-100.

EXAMPLE 6

In a similar manner, a 10% solution of a pharmaceutical grade of chondroitin sulfate supplied by Seikagaku Corporation was acidified and dialyzed in tubing having a molecular weight cutoff of 3500. The product gave a negative silver nitrate test for chloride ion, had a pH of 3.7, and was colorless and sparkling clear.

EXAMPLE 7

A 1% aqueous solution of sodium carboxymethyl cellulose was prepared and found to have a viscosity of 22 poises. It was acidified with 3.7 grams of 1 Normal HCl per 100 grams of solution and dialyzed in a membrane having a molecular weight cutoff of 3500. On the third day, after five water changes, the pH of the external water was 6.2 and the product was harvested. The product gave a negative test for chloride ion and had a pH of 3.4 and a viscosity of 2 poises. When mixed with CX-100, knife-coated onto an acrylic panel which had been coated with an acrylic acid copolymer, and heated at 60° C., the film became water-insoluble, but water spread evenly over the surface of the cured film and did not show beading. This is a desirable result, insofar as it shows that the coating does not dissolve in water, and is properly grafted to the underlying substrate. The composite film, when completely cured, was lubricious and hydrophilic.

The reader skilled in the art will recognize other variations of the method. Such variations should be considered within the spirit and scope of the following claims.

What is claimed is:

1. A method for converting an alkali-metal salt of hyaluronic acid to a free acid form of hyaluronic acid, the method comprising the steps of:
    a) dissolving an alkali-metal salt of hyaluronic acid in water to form a solution,
    b) dispersing in said solution an acid capable of producing a pH of 2.2 or lower at concentrations in water at 25° C. of 0.01 Normal to 1 Normal,
    c) enclosing the dispersion formed in step (b) within a semi-permeable membrane having a molecular weight cut-off at least large enough to pass said acid,
    d) dialyzing the dispersion in water while the dispersion is so enclosed, and e) harvesting free hyaluronic acid from within the semi-permeable membrane.

2. The method of claim 1, wherein the acid added in step (b) is an acid selected from the group consisting of hydrochloric acid, sulfuric acid, nitric acid, orthophosphoric acid, and oxalic acid.

3. The method of claim 1, wherein the semi-permeable membrane is made from a material selected from the group consisting of regenerated cellulose and cellulose esters.

4. The method of claim 1, wherein the molecular weight cut-off of the semi-permeable membrane is at least twice as great as that needed to pass the acid added in step (b).

5. The method of claim 1, wherein the ratio of volume of the water used to dialyze in step (d), to the volume of the hyaluronate solution, is 5:1 or less.

6. The method of claim 1, wherein the steps are performed at a temperature in the range of about 4°–30° C.

7. The method of claim 1, wherein the dialyzing step is performed until water surrounding the membrane has a predetermined pH.

8. A method for converting a salt of a polysaccharide to a free acid form of the polysaccharide, the method comprising the steps of:

a) dissolving a salt of a polysaccharide in water to form a solution, b) dispersing an acid in said solution, c) enclosing the dispersion formed in step (b) within a semi-permeable membrane, d) dialyzing the dispersion in water while the dispersion is so enclosed, and e) harvesting a free acid form of the polysaccharide from within the semi-permeable membrane.

9. The method of claim 8, wherein the polysaccharide salt is sodium hyaluronate.

10. The method of claim 8, wherein the acid added in step (b) is an acid selected from the group consisting of hydrochloric acid, sulfuric acid, nitric acid, orthophosphoric acid, and oxalic acid.

11. The method of claim 8, wherein the semi-permeable membrane has a molecular weight cut-off large enough to pass the acid added in step (b).

12. The method of claim 11, wherein the semi-permeable membrane is made from a material selected from the group consisting of regenerated cellulose and cellulose esters.

13. The method of claim 11, wherein the molecular weight cut-off of the semi-permeable membrane is at least twice as great as that needed to pass the acid added in step (b).

14. The method of claim 8, wherein the ratio of volume of the water used to dialyze in step (d), to the volume of the solution of step (b), is 5:1 or less.

15. The method of claim 8, wherein the steps are performed at a temperature in the range of about 4°–30° C.

16. The method of claim 8, wherein the dialyzing step is performed until water surrounding the membrane has a predetermined pH.

17. The method of claim 8, wherein the polysaccharide is selected from the group consisting of chondroitin sulfate, heparin, and carboxymethyl cellulose.

18. A method of making free hyaluronic acid, the method comprising the steps of:

a) preparing a solution of sodium hyaluronate in distilled water, b) mixing into said solution an acid capable of producing a pH of 2.2 or lower at concentrations in water at 25° C. in the range of 0.01 Normal to 1 Normal, to produce a mixture, c) enclosing said mixture in a dialysis bag having a molecular weight cut-off large enough to pass the acid added in step (b), d) placing the bag in de-ionized water, d) periodically replacing the de-ionized water with fresh de-ionized water, until the pH of the de-ionized water exceeds 5.0, and e) harvesting free hyaluronic acid from within the bag.

19. The method of claim 18, wherein the acid added in step (b) is hydrochloric acid.

20. The method of claim 18, wherein the molecular weight cut-off of the bag is 3500.

* * * * *